United States Patent [19]

Blair

[11] Patent Number: 5,304,145
[45] Date of Patent: Apr. 19, 1994

[54] GASTRONOMY TUBE HOLDER

[76] Inventor: Jacqueline E. Blair, 85 Homeward Ave., Uxbridge, Mass. 01569

[21] Appl. No.: 27,434

[22] Filed: Mar. 8, 1993

[51] Int. Cl.⁵ .............................................. A61M 5/32
[52] U.S. Cl. .............................. 604/179; 128/DIG. 6; 604/174
[58] Field of Search ............... 604/345, 174, 179, 180; 128/DIG. 6, DIG. 26

[56] References Cited

U.S. PATENT DOCUMENTS

| 3,022,786 | 2/1962 | Nalon | 604/345 |
|---|---|---|---|
| 4,096,853 | 6/1978 | Weigand | 604/179 |
| 4,191,180 | 3/1980 | Colley et al. | 128/207.17 |
| 4,610,245 | 9/1986 | Biearman | 604/179 |
| 4,666,432 | 5/1987 | McNeish et al. | 604/179 |
| 4,799,923 | 1/1989 | Campbell | 604/179 |
| 4,897,082 | 1/1990 | Erskine | 604/180 |
| 5,048,512 | 9/1991 | Turner et al. | 604/179 |
| 5,116,324 | 5/1992 | Brierley et al. | 604/174 |
| 5,135,519 | 8/1992 | Helmer | 604/345 |
| 5,147,320 | 9/1992 | Reynolds et al. | 604/174 |

Primary Examiner—Paul J. Hirsch
Attorney, Agent, or Firm—Leon Gilden

[57] ABSTRACT

A gastronomy tube holder arranged for ease of access and employment is provided to include a belt member arranged for torso mounting relative to an individual, having cooperative support and cover plate structure to secure in a sanitized convenient manner a gastronomy tube for subsequent use, with a slot directed through the support plate for access into the individual for use.

1 Claim, 4 Drawing Sheets

GASTRONOMY TUBE HOLDER

BACKGROUND OF THE INVENTION

1. Field of the Invention

The field of invention relates to medical tube support structure, and more particularly pertains to a new and improved gastronomy tube holder arranged for storage and orientation relative to an individual.

2. Description of the Prior Art

The use of gastronomy tubes for individuals is available in the prior art, wherein such devices are typically related to holding structure for gastronomy tubes, wherein feeding of the individual must be directed through a tube structure into the intestinal tract or stomach portion such that a portion of the gastronomy tube projects from the patient and individual for reception of a food substance where food may not be consumed orally. Gastronomy tube structure per se is known in the prior art where such gastronomy tubes typically employ a tube structure tape to the body, wherein the instant invention is directed to the use of a tube structure mounted within an easy storage container relative to the associated belt for use by an individual.

SUMMARY OF THE INVENTION

In view of the foregoing disadvantages inherent in the known types of tube holder apparatus now present in the prior art, the present invention provides a gastronomy tube holder wherein the same is directed for the transport and storage and orientation for use of a gastronomy tube. As such, the general purpose of the present invention, which will be described subsequently in greater detail, is to provide a new and improved gastronomy tube holder which has all the advantages of the prior art tube holder apparatus and none of the disadvantages.

To attain this, the present invention provides a gastronomy tube holder arranged for ease of access and employment, to include a belt member arranged for torso mounting relative to an individual, having cooperative support and cover plate structure to secure in a sanitized convenient manner a gastronomy tube for subsequent use, with a slot directed through the support plate for access into the individual for use.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved gastronomy tube holder which has all the advantages of the prior art tube holder apparatus and none of the disadvantages.

It is another object of the present invention to provide a new and improved gastronomy tube holder which may be easily and efficiently manufactured and marketed.

It is a further object of the present invention to provide a new and improved gastronomy tube holder which is of a durable and reliable construction.

An even further object of the present invention is to provide a new and improved gastronomy tube holder which is susceptible of a low cost of manufacture with regard to both materials and labor, and which accordingly is then susceptible of low prices of sale to the consuming public, thereby making such gastronomy tube holders economically available to the buying public.

Still yet another object of the present invention is to provide a new and improved gastronomy tube holder which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
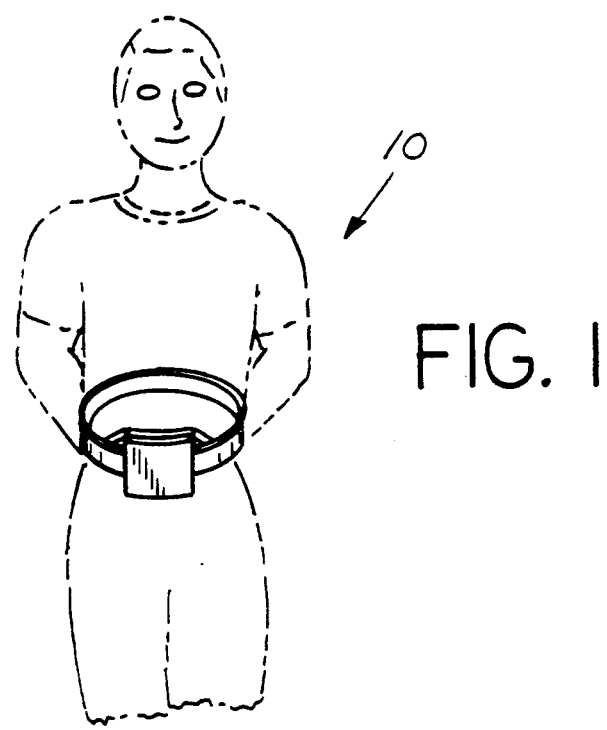
FIG. 1 is an isometric illustration of the invention in use.

With reference now to the drawings, and in particular to FIGS. 1 to 8 thereof, a new and improved gastronomy tube holder embodying the principles and concepts of the present invention and generally designated by the reference numeral 10 will be described.

Figure 2:
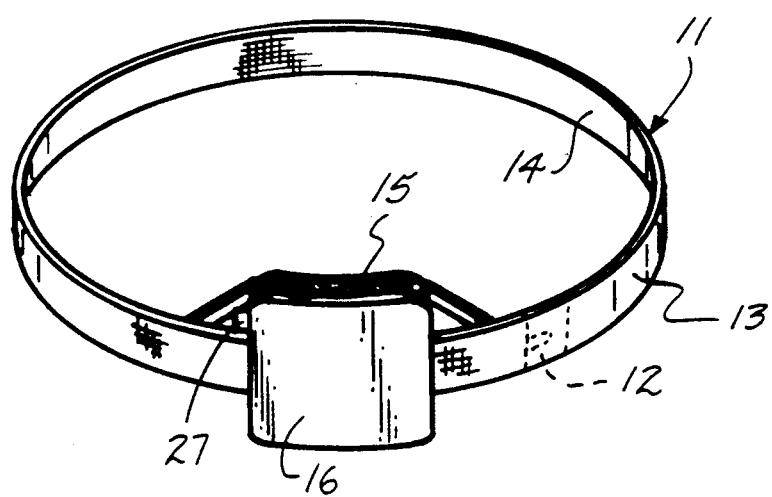
FIG. 2 is an isometric illustration of the invention.
Figure 3:
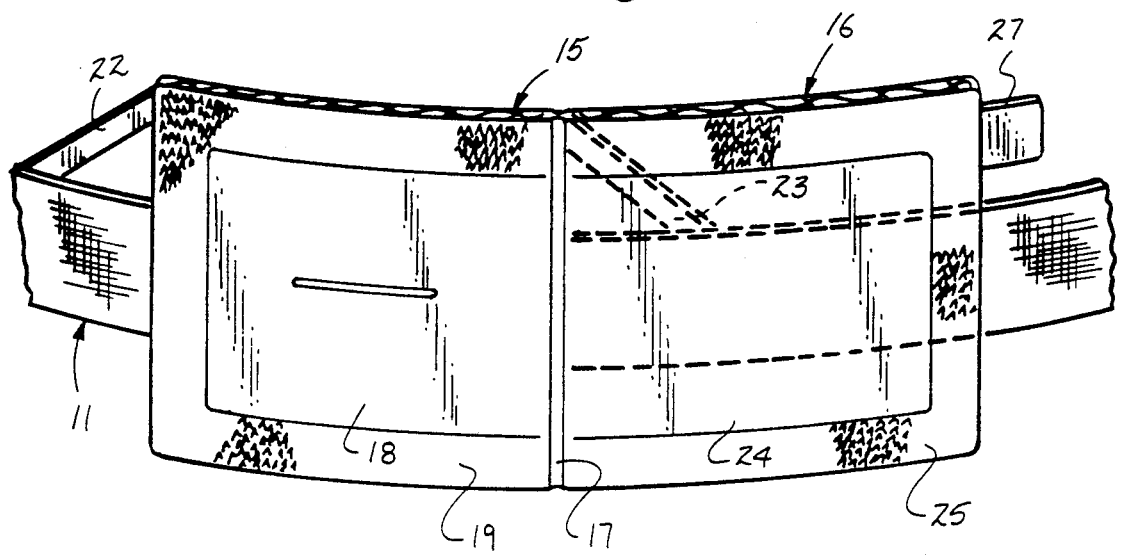
FIG. 3 is an enlarged isometric illustration of the cover plate pivotally opened relative to the support plate.
Figure 4:
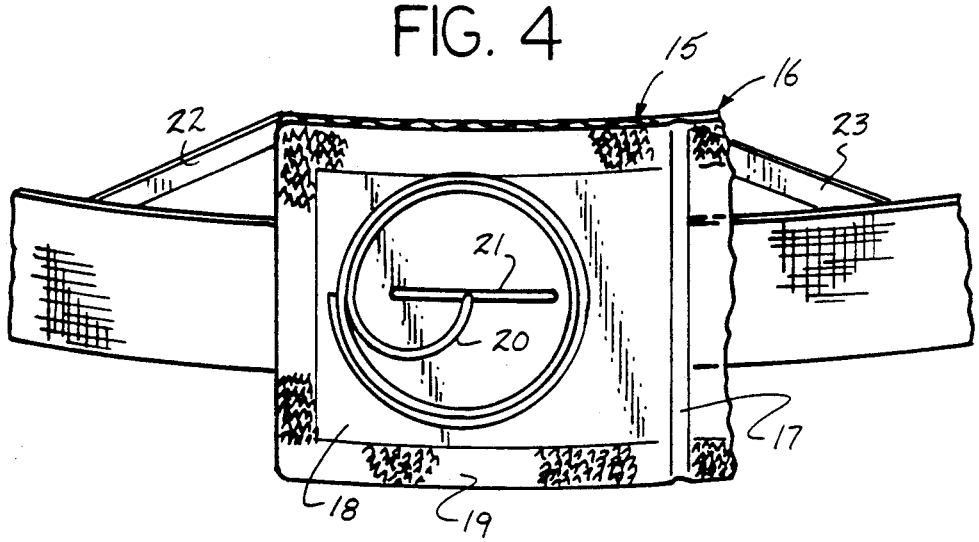
FIG. 4 is an isometric illustration of the support plate structure having a gastronomy tube positioned therewithin.

More specifically, the gastronomy tube holder 10 of the instant invention essentially comprises a belt member 11, typically elastomeric but may be formed of a flexible material to include a buckle 12 as desired about the belt for its ease of disassembly and reassembly. The belt 11 is formed with a belt outer wall 13 and a belt inner wall 14, with the belt outer wall having a support plate 15 fixedly mounted thereon. The support plate 15 includes respective first and second support ribs 22 and 23 (see FIG. 4) extending from the support plate to the belt 11. The support plate includes a support plate front wall 18 having a first hook and loop fastener strip 19 mounted thereon arranged to receive a gastronomy tube 20 of a flexible tubular construction stored in a coiled orientation, as indicated in FIG. 4, but arranged for projection through a slot 21 directed through the support plate front wall 18 for access to the patient requiring such gastronomy tube use. A cover plate 16 is provided hingedly mounted to the support plate 15 about a hinge 17, with the cover plate 16 including a cover plate rear wall 24 having a second hook and loop fastener strip 25 arranged for complementary and contiguous communication with the first hook and loop fastener strip 19 to secure the cover plate 16 to the support plate 15, in a manner as indicated in FIG. 2.

Figure 5:
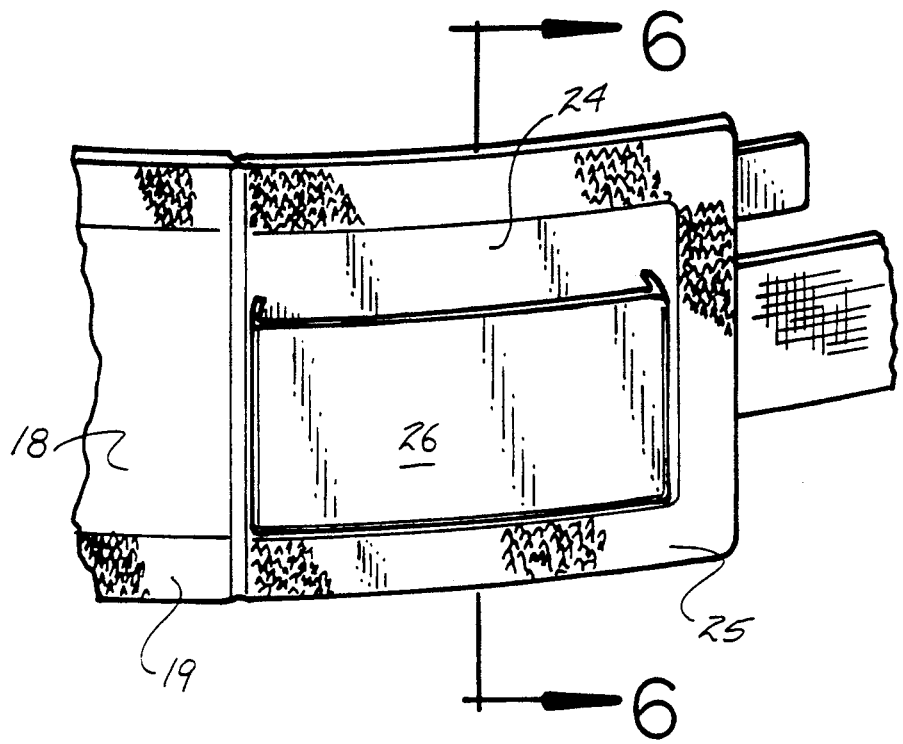
FIG. 5 is an enlarged isometric illustration of the support plate including a pocket member.
Figure 6:
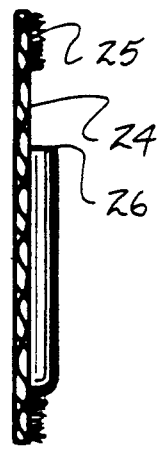
FIG. 6 is an orthographic view, taken along the lines 6—6 of FIG. 5 in the direction indicated by the arrows.

The FIG. 5 indicates the use of an optional pocket member 26 of a flexible construction mounted to the cover plate rear wall 24 to receive and store a spare gastronomy tube, hypodermic needles as required, and the like.

It should be noted that a rigid lift flange 27 is mounted to the cover plate 16 in an integral association therewith for ease of grasping of the cover plate to permit ease of displacement of the cover plate relative to the support plate for access to the gastronomy tube.

Figure 7:
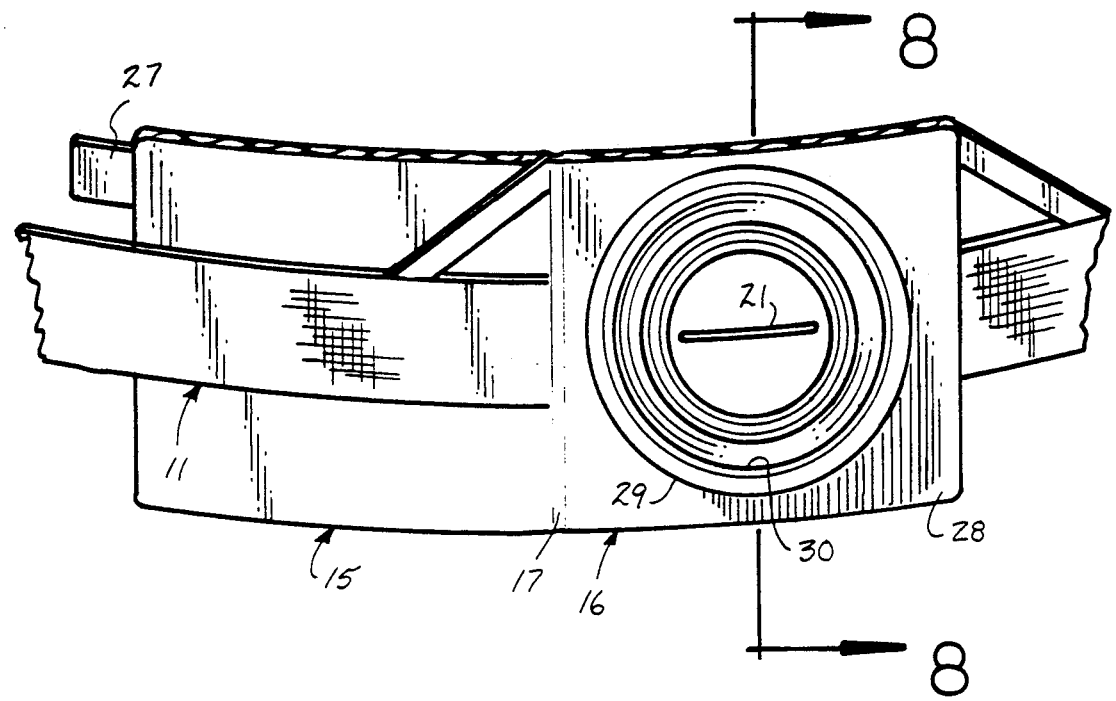
FIG. 7 is an isometric rear view of the support plate structure to employ a sealing ring.
Figure 8:
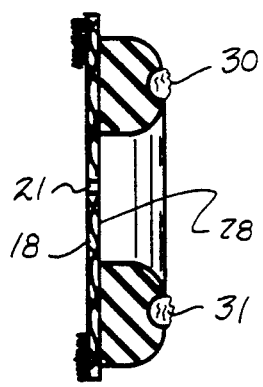
FIG. 8 is an orthographic view, taken along the lines 8—8 of FIG. 7 in the direction indicated by the arrows.

The FIGS. 7 and 8 indicate the use of a sealing ring of continuous annular construction indicated as a numeral 29 in FIGS 7 and 8. The sealing ring 29 is mounted to the support plate rear wall 28 for contiguous communication to the individual for sanitary sealing of the slot 21 that is surroundingly oriented by the sealing ring 29. Further, an annular groove 30 is provided within the sealing ring 29 to receive an inert sealing cream 31, such as VASELINE (®) to enhance sealing of the gastronomy tube to the patient through the slot 21.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A gastronomy tube holder, comprising,
    a belt member, the belt member having an interior surface and an exterior surface, with the exterior surface including a support plate fixedly mounted to the exterior surface, and
    a cover plate, and
    a hinge, with the hinge interconnecting the support plate to the cover plate, wherein the cover plate is arranged in a coextensive relationship relative to the support plate in a first position and displaced relative to the support plate in a second position, and
    the support plate having a support plate front surface and a support plate rear surface, the support plate rear surface mounted to the belt exterior surface, and the support plate front surface including a first hook and loop fastener strip, the cover plate including a cover plate front surface and a cover plate rear surface, the cover plate rear surface including a second hook and loop fastener strip arranged for securement to the first hook and loop fastener strip, and
    a slot directed through the support plate, and
    a gastronomy tube positioned about the slot on the support plate front surface, and
    a first support rib and a second support rib fixedly mounted on opposed sides of the support plate extending from the support plate to the belt, and
    the cover plate rear surface includes a flexible pocket member, and
    a lift flange is fixedly mounted to the cover plate extending beyond the cover plate for ease of manual grasping of the lift flange for displacement of the cover plate to the second position, and
    an annular resilient ring is arranged in surrounding relationship relative to the slot, with the resilient ring mounted to the support plate rear surface, and the resilient ring includes a continuous annular groove for reception of an inert sealing cream therewithin.

* * * * *